United States Patent [19]
Fischell et al.

[11] Patent Number: 5,334,187
[45] Date of Patent: Aug. 2, 1994

[54] BALLOON CATHETER SYSTEM WITH SLIT OPENING HANDLE

[75] Inventors: Robert E. Fischell, Dayton, Md.; David R. Fischell, Fair Haven, N.J.; Tim A. Fischell, Nashville, Tenn.

[73] Assignee: Cathco, Inc., Dayton, Md.

[21] Appl. No.: 98,439

[22] Filed: Jul. 28, 1993

Related U.S. Application Data

[63] Continuation-in-part of Ser. No. 65,593, May 21, 1993.

[51] Int. Cl.⁵ ............................................. A61M 25/00
[52] U.S. Cl. .................................... 604/194; 604/102; 604/160
[58] Field of Search .................. 604/96, 102, 159, 160, 604/161, 165; 606/192, 194

[56] References Cited

U.S. PATENT DOCUMENTS

| | | | |
|---|---|---|---|
| 4,748,982 | 6/1988 | Horzewski et al. | 128/344 |
| 4,988,356 | 1/1991 | Crittenden et al. | 606/192 |
| 5,061,273 | 10/1991 | Yocz | 606/194 |
| 5,135,535 | 8/1992 | Kramer | 606/194 |
| 5,171,222 | 12/1992 | Euteneuer et al. | 604/102 |
| 5,205,822 | 4/1993 | Johnson et al. | 604/96 |

FOREIGN PATENT DOCUMENTS 8603129  6/1986  World Int. Prop. O. .

*Primary Examiner*—John D. Yasko
*Assistant Examiner*—Anthony Gutowski

[57] ABSTRACT

A balloon angioplasty catheter system comprising a flexible guide wire, balloon catheter and slide handle. The balloon catheter has a shaft with a guide wire lumen that includes a guide wire removal slit which extends along a portion of the shaft. The slide handle is configured to open the slit as the handle slides along the catheter. The handle includes a separate passage for the catheter and guide wire and is provided with a fitting for connecting the handle to the "Y" adaptor of a guide catheter. The system provides a arrangement with the advantages of both an over-the-wire and monorail catheter.

7 Claims, 6 Drawing Sheets

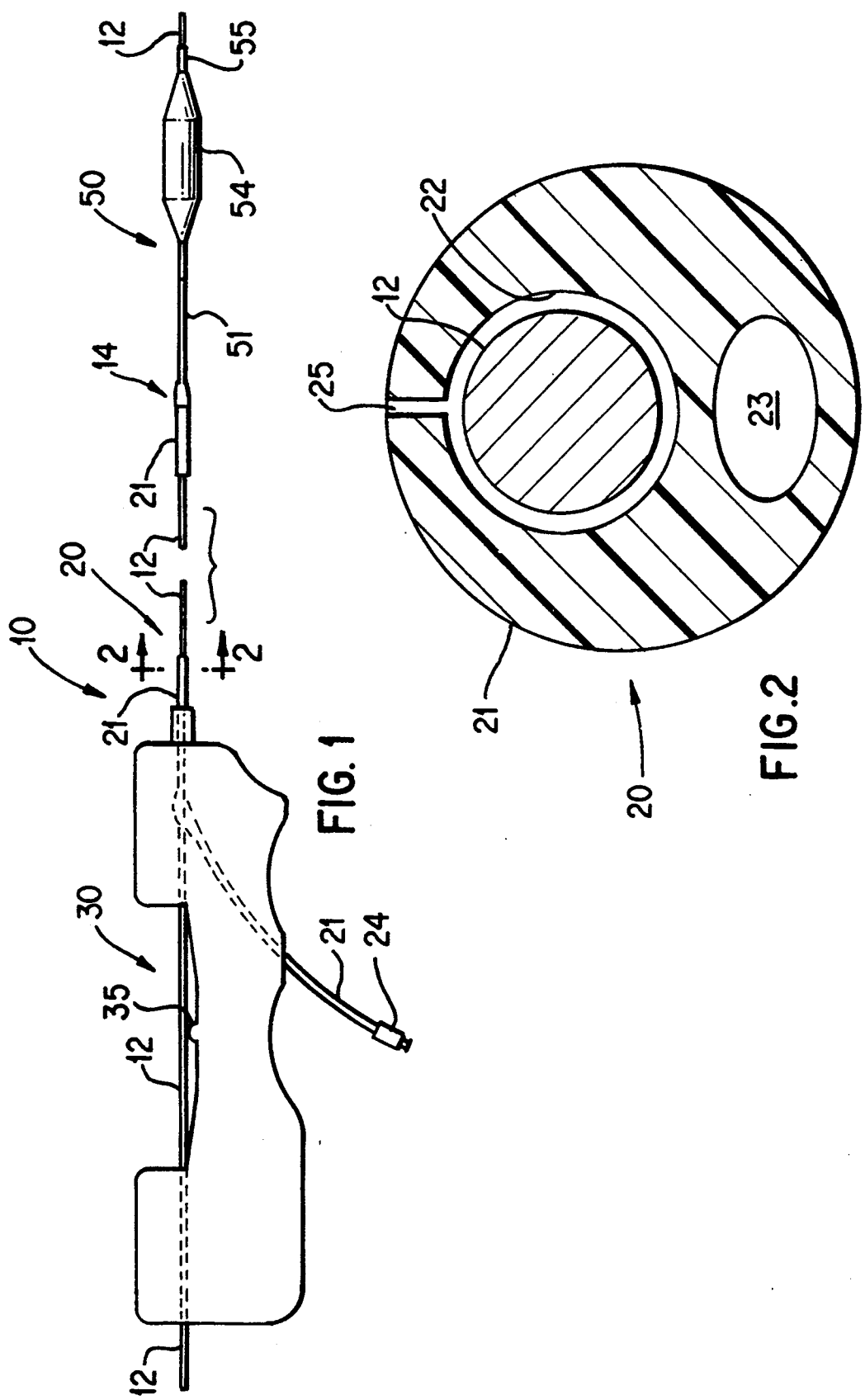

BALLOON CATHETER SYSTEM WITH SLIT OPENING HANDLE

REFERENCE TO RELATED APPLICATION

This application is a continuation-in-part of patent application Ser. No. 08/065,593, filed on May 21, 1993.

FIELD OF USE

This invention is in the field of catheters to perform Percutaneous Transluminal Coronary Angioplasty (PTCA).

BACKGROUND OF THE INVENTION

One type of PTCA catheter, called an "over-the-wire" balloon angioplasty catheter, is characterized by having a lumen or passageway throughout its entire length which is adapted for the free movement of a guide wire, which guide wire exits at the catheter's proximal end lying outside of the patient's body.

A second type of PTCA catheter called a "monorail" balloon angioplasty catheter is characterized by having a guide wire passageway that extends within only a comparatively short distal segment of the catheter. The monorail catheter's proximal exit port for the guide wire typically lies approximately 10 inches proximal to the catheter's distal end.

The capabilities of the over-the-wire and monorail types of the catheters are presented in Table 1.

TABLE 1

| CAPABILITY | OVER-THE-WIRE | MONO-RAIL |
| --- | --- | --- |
| 1. Advance balloon catheter over a conventional length guide wire already placed in a coronary artery ("bare wire" technique) | NO | YES |
| 2. Perform catheter exchange without requiring an extension guide wire or a trapping catheter | NO | YES |
| 3. A single operator can perform a rapid exchange procedure without requiring a guide wire trapping device | NO | YES |
| 4. Guide wire exchange with balloon catheter placed across the stenosis (guide wire exchange capability) | YES | NO |
| 5. A single operator can easily perform the entire balloon angioplasty procedure without an assistant | NO | YES |
| 6. A single operator can rapidly perform the final 20–25 cm of catheter removal without requiring a guide wire trapping device | NO | NO |
| 7. Easy and precise control of guiding catheter-balloon catheter interactions at right or left coronary ostium without jeopardizing the position of the guide wire within the coronary artery | YES | NO |
| 8. Advancement of PTCA catheter shaft through the Tuohy-Borst fitting (attached to guiding catheter) unencumbered by a guide wire lying outside of the balloon catheter shaft | YES | NO |
| 9. Either over-the-wire or monorail capabilities are available at any time during an angioplasty procedure while using only one balloon catheter | NO | NO |

It should be noted that each design has some significant shortcomings.

SUMMARY OF THE INVENTION

The Dual Modality Balloon Angioplasty Catheter (DMBAC) of the present invention is designed to overcome the shortcomings of both the over-the-wire and monorail designs of balloon angioplasty catheters. Specifically, the DMBAC can function with the capabilities of either an over-the-wire or a monorail design. For example, when used with only a conventional (short) guide wire, rapid catheter exchange can be accomplished by operating the DMBAC as a monorail type catheter. If guide wire exchange is required, this can be accomplished by using the DMBAC as an over-the-wire type catheter. The DMBAC also includes a unique slide handle mechanism which allows a single operator to rapidly and conveniently remove the last 10 inches of the DMBAC catheter from the guiding catheter when operated in the monorail mode. Specifically, a thumb-motion operated mechanism on the slide handle allows the guide wire to be readily advanced relative to the catheter shaft using one hand while the shaft of the DMBAC catheter and the slide handle itself are simultaneously being withdrawn from the guiding catheter with that same hand. The operator's other hand is used at that time to hold the "Y" adaptor which is attached to the guiding catheter's proximal end.

Thus, an object of this invention is to have a single PTCA catheter which can function as either an over-the-wire or as a monorail type catheter depending on how the operator chooses to use it.

Another object of this invention is that, at any time during a PTCA procedure, the operator can elect to change the modality of catheter use from an over-the-wire mode to a monorail mode or visa versa without removing the PTCA catheter from the guiding catheter.

Still another object of this invention is to provide a novel means for the rapid exchange of the last approximately 10 inches of the DMBAC from the guiding catheter when it is operated in the monorail mode.

Still another object of this invention is to allow a single operator without an assistant to completely perform a PTCA procedure including the capability of guide wire exchange.

Still another object of this invention is to provide a slide handle through which a guide wire and/or PTCA balloon catheter shaft can slide; this slide handle being able to be attached to the proximal end of a "Y" adaptor which is attached at its distal end to a guiding catheter so that with one hand a single operator can control the guiding catheter, the guide wire and the balloon catheter shaft.

Still another object of this invention is that the guide wire is held straight within the slide handle to optimize guide wire torquing.

These and other objects and advantages of this invention will become apparent upon careful reading of the detailed description of this invention as presented herein.

BRIEF DESCRIPTION OF THE DRAWINGS

FIG. 1 is a longitudinal side view of the DMBAC catheter.

FIG. 2 is a highly enlarged transverse cross section of the shaft of the DMBAC at section 2—2 of FIG. 1.

DETAILED DESCRIPTION OF THE DRAWINGS

Figure 3:
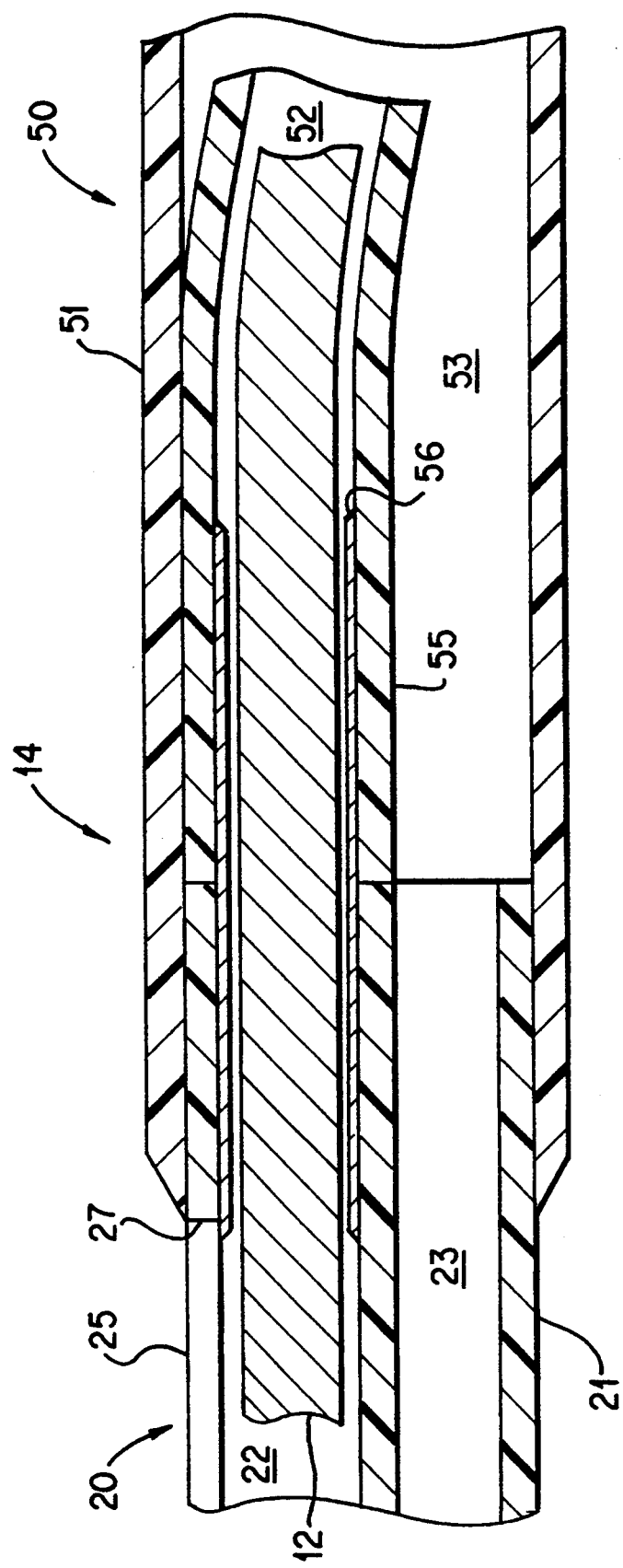
FIG. 3 is a longitudinal cross section of the transition section of the DMBAC.

FIG. 1 illustrates each major subsystem of the DMBAC 10. Specifically, the DMBAC 10 consists of a guide wire 12, a catheter shaft 20, a slide handle 30, a transition section 14 and a distal balloon angioplasty catheter segment 50. The distal segment 50 consists of an outer shaft 51, an inner shaft (not shown) and a dilation balloon 54. The purpose of this PTCA catheter (the DMBAC 10) is to dilate a stenosis in a coronary (or other) artery. The distal segment 50 is joined to the shaft body 21 by the transition section 14. The distal segment 50 would typically be a coaxial design which is well known in the art of PTCA balloon catheters. Specifically, the coaxial design has an elongated inner shaft through which a guide wire is placed and an outer shaft 51 that surrounds the inner shaft; the space between the two shafts constituting an annular lumen through which balloon inflation/deflation fluid can pass. The proximal end of the balloon 54 is typically joined to the distal end of the outer shaft 51, and the distal end of the balloon 54 is joined to the distal end of the inner shaft 55.

The shaft 20 of the DMBAC 10 has a shaft body 21 and a proximal Luer lock adaptor 24 through which the dilatation balloon 54 can be inflated or deflated.

FIG. 2 shows a highly enlarged transverse cross section of the shaft 20 of the DMBAC 10. Specifically, the shaft 20 has an extruded plastic body 21, a guide wire lumen 22, a balloon inflate/deflate lumen 23 and a slit 25. Also shown in FIG. 2 is the cross section of the guide wire 12 as it passes through the guide wire lumen 22. Although the cross section of FIG. 2 is certainly one embodiment for this invention, other cross sections, e.g. using a thin-walled metal tube surrounded by a slit plastic tube is also envisioned.

FIG. 3 illustrates the transition section 14 which joins the distal end of the shaft 20 to the proximal end of the segment 50. To effect this transition, a very thin-walled cylindrical tube 56 is placed within and is adhesively joined to the guide wire lumen 22 of the shaft body 21. A short length inside the inner shaft 55 of the distal segment 50 is adhesively joined to the outside of the tube 56 as shown in FIG. 3. A short length of the outer surface of the tube body 21 at its distal end is simultaneously adhesively joined to a short length inside the proximal end of the outer shaft 51. Balloon inflation/deflation fluid can then flow from the lumens 23 and 53 into the interior of the balloon 54, and the guide wire 12 can pass through the guide wire lumen 22, the interior passageway of the tube 56 and also the lumen 52 of the inner shaft 55. Also shown in FIG. 3 is the slit 25 of the shaft body 21 which has a distal terminus 27 situated at the proximal end of the transition section 14.

Figure 4A:
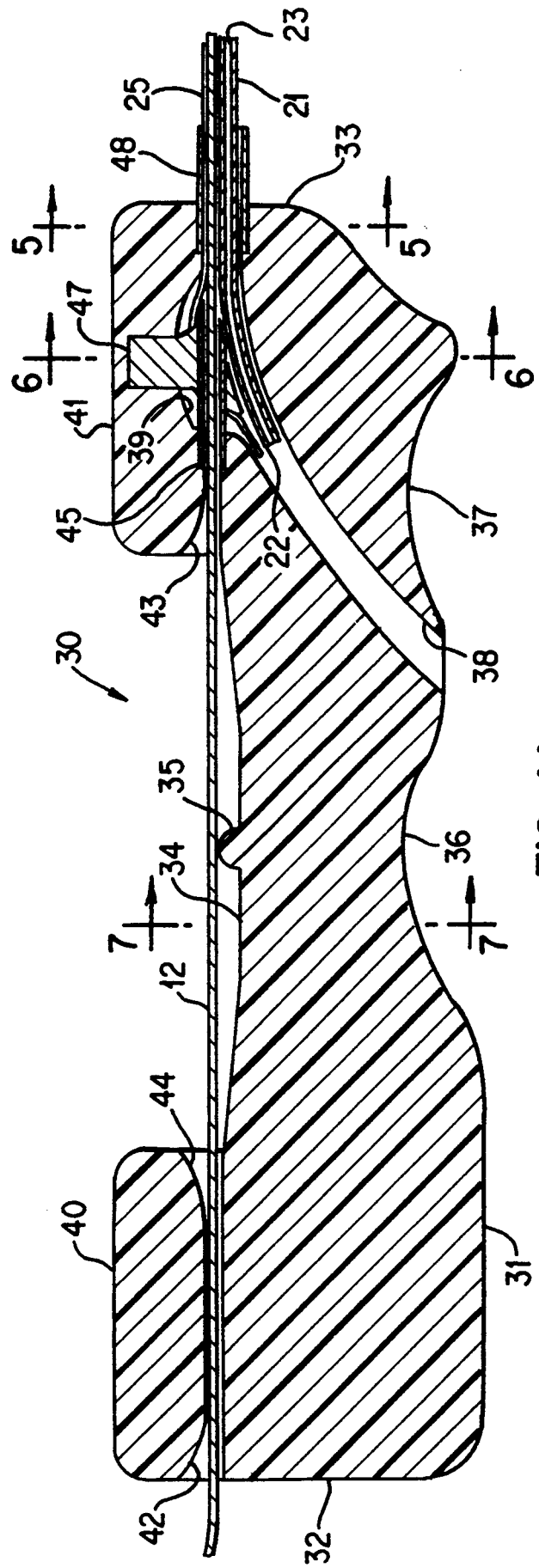
FIG. 4A is an enlarged longitudinal cross section of the slide handle of the DMBAC.

FIG. 4A shows an enlarged longitudinal cross section of the slide handle 30 of the DMBAC 10. The handle 30 has a body 31, a proximal end 32, a distal end 33, a top concave surface 34 having a transverse ridge 35 and bottom indentations 36 and 37 which assist in providing a comfortable grip for the operator's fingers. The handle 30 also has a through lumen 38 which is a passageway for the shaft body 21 of the DMBAC 10. An enlarged chamber 39 whose function will later be described is also shown in FIG. 4A. A slit opening member 47 which supports a guide wire tube 45 is fixedly attached to the slide handle body 31.

At the top of the handle 30 is a proximal top section 40 having a tapered proximal port 42 and a tapered distal port 44. The handle 30 also has a distal top section 41 having a tapered port 43. When the guide wire 12 is fed through the handle 30 from its proximal end 32, the guide wire 12 first passes through the port 42, then out the port 44, then over the top concave outer surface 34 with ridge 35, then into the port 43, then through the thin-walled metal guide wire tube 45 and finally into the guide wire lumen 22 of the shaft body 21. Thus there is a complete guide wire passageway through the slide handle 30. When the distal end of the DMBAC 10 is advanced over a guide wire 12 that has been placed through an arterial stenosis, the handle is first advanced forward (outside of the body) until it is stopped by the distal terminus 27 of the slit 25. The proximal end of the guide wire 12 is then placed through the distal segment 50 (see FIG. 1), through the transition section 14 then through the guide wire lumen 22 of the shaft body 21 and then through the metal tube 45, out the port 43, then over the top concave outer surface 34 with ridge 35, into the port 44 and finally emerging from the port 42. This entire passageway is equivalent to the guide wire lumen of an over-the-wire PTCA catheter.

The procedure to load the DMBAC 10 with the guide wire 12 from the DMBAC's proximal end 32, can be performed with the slide handle 30 in any position with respect to the shaft 20. The guide wire 12 is first pushed through the port 42, out the port 44, then over the concave outer surface 34 with ridge 35, into the port 43, through the tube 45 and into the guide wire lumen 22 of the shaft body 21. The operator can then advance the guide wire 12 by using the thumb of one hand to push down on the guide wire 12 where it lies over the ridge 35 by moving the thumb in a forward direction while holding the slide handle and the shaft body 21 in the operator's same hand. By successively moving his thumb in the forward direction, removing his thumb from the guide wire 12, and moving his thumb to the proximal end of the concave surface 34 and then pushing the guide wire 12 over the ridge 35 while advancing it once more in the forward direction, the guide wire 12 can be readily advanced through the DMBAC 10 until its distal end barely extends beyond the distal end of the DMBAC 10. The DMBAC 10 can then be placed through a guiding catheter that has previously been placed through an introducer sheath in the groin and into the ostium of a coronary artery. This is exactly the type of operation that can be performed with an over-the-wire balloon catheter. When the angioplasty procedure is completed, the DMBAC 10 including the guide wire 12 can be pulled out of the guiding catheter in a manner exactly like an over-the-wire balloon catheter.

It should be noted in FIG. 4A that the guide wire 12 lies straight within the passageways through the slide handle 30. This straightness optimizes the operator's ability to torque the guide wire 12 so as to readily manipulate the advancement of the guide wire's distal end.

Figure 4B:
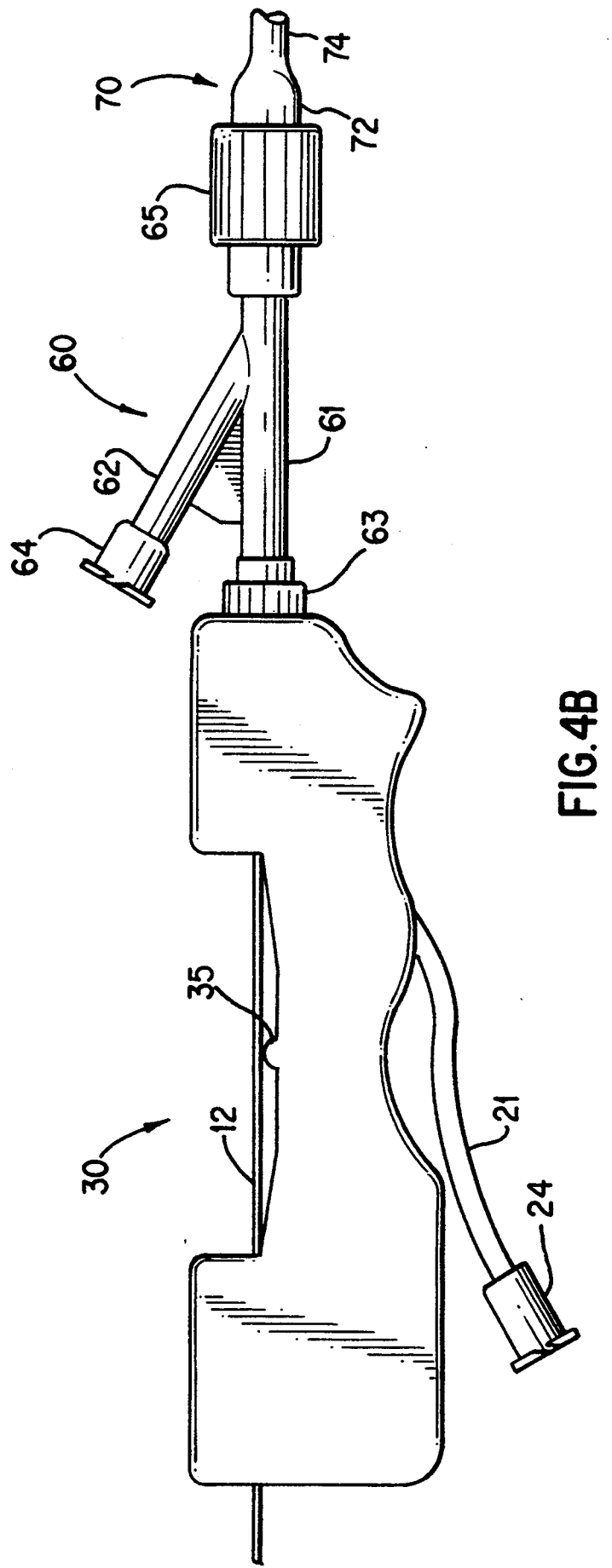
FIG. 4B illustrates the slide handle attached to a "Y" adaptor which is attached to a guiding catheter.

FIG. 4B illustrates the handle 30 through which the guide 12 passes over the ridge 35 and through which passes the catheter body 21 having a proximal Luer lock fitting 24. FIG. 4B also shows a "Y" adaptor 60 having a Tuohy-Borst fitting 63 on a first leg 61, a Luer fitting 64 on a second leg 62, and a male Luer lock fitting 65 which can be secured to the female Luer lock fitting 72 at the proximal end of the guiding catheter 70 which has an elongated body 74. The Luer lock fitting 64 is typically joined to a manifold (not shown) which can be used to inject contrast medium or medication through the guiding catheter 70 and into the patient. The thin-walled, metal tube 48 located at the distal end 33 of the handle 30 as shown in FIG. 4A, can be securely inserted into the Tuohy-Borst fitting 63 of the "Y" adaptor 60 (shown in FIG. 4B) that is attached to the proximal end of the guiding catheter 70. This allows a single operator to control the guide wire 12, the "Y" adaptor 60 and the guiding catheter 70 all with only one hand. The operator can then use his other hand to separately manipulate the shaft body 21.

If it is desired to exchange the guide wire 12 for another guide wire, this can be accomplished while leaving the distal end of the DMBAC 10 within the stenosis of a coronary artery. To accomplish this maneuver, the operator holds the shaft body 21 and slide handle 30 in one hand while pulling back on the proximal end of the guide wire 12 to remove it from the catheter lumen 22. An exchange guide wire can then be advanced through the port 42, out the port 44, into the port 43, through the tube 45 and into the guide wire lumen 22 of the shaft body 21 and finally out of the distal end of the DMBAC 10. Thus, guide wire exchange can be accomplished in a manner analogous to an over-the-wire balloon catheter.

If it is desired to retain the guide wire 12 though an arterial stenosis while exchanging the DMBAC 10 for a new balloon angioplasty catheter or another type of catheter, the operator can pull back the shaft body 21 from either side of the slide handle 30 while holding the handle body 31 and pushing with his thumb down onto the guide wire 12 where it is located above the ridge 35 in order to prevent the guide wire 12 from moving. When doing this procedure, the distal end of the tube 45 and the slit opening member 47 will open the slit 25 of the shaft body 21. The guide wire 12 will remain stationary relative to the arterial stenosis while the shaft body 21 is pulled back out of the guiding catheter. When the distal terminus 27 of the slit 25 (see FIG. 3) is finally reached, (with the distal segment 50 still remaining within the guiding catheter), the Tuohy-Borst fitting 63 (see FIG. 4B) is opened and the distal metal tube 48 (see FIG. 4A) is pulled out of the "Y" adaptor 60. The guide wire 12 is then advanced relative to the handle 30 using the thumb of one of the operator's hands while the operator pulls back on the shaft 21 and the handle 30 with that same hand while holding the "Y" adaptor in his other hand. This procedure is continued until the entire distal segment 50 (typically 25 cm long) is removed from the guiding catheter while the guide wire 12 remains in place across the arterial stenosis. Another DMBAC type of catheter can then be advanced over the guide wire 12 (i.e. in the distal direction) by first moving the slide handle 30 to its full forward position relative to the shaft body 21 and then feeding the guide wire 12 through the distal end of the distal segment 50, then through the inner coaxial lumen 52, through the guide wire lumen 22, through the tube 45, out the port 43, into the port 44 and finally out of the port 42. The distal metal tube 48 can then be pushed into the first leg 61 of the "Y" adaptor 60 and the Tuohy-Borst fitting 63 can be tightened to securely join the handle 30 to the guiding catheter 70 via the "Y" adaptor 60. The operator can then hold the handle 30 in one hand while using the thumb of that hand to secure the guide wire 12 securely against the ridge 35. While thus holding the guide wire 12 in a fixed position relative to the arterial stenosis, the shaft body 21 can be advanced over the guide wire 12 until the balloon 54 of the distal segment 50 is placed through the stenosis. Thus, a single operator rapid exchange has been accomplished without requiring an exchange guide wire 12, which is exactly the procedure that can be performed with a monorail balloon catheter but not with an over-the-wire design. Thus, it has been shown that at any time during a procedure, and only using a short (conventional) guide wire, the DMBAC 10 can operate either in the over-the-wire mode or the monorail mode.

FIGS. 4C, 5, 6 and 7 illustrate highly enlarged longitudinal and transverse cross sections of the handle 30, shaft body 21 and guide wire 12. The slit opening members 47 and 49 prevent rotation of the shaft body 21 as it slides in a forward or backward direction relative to the shaft 20 and within the guide wire lumen 22.

Figure 4C:
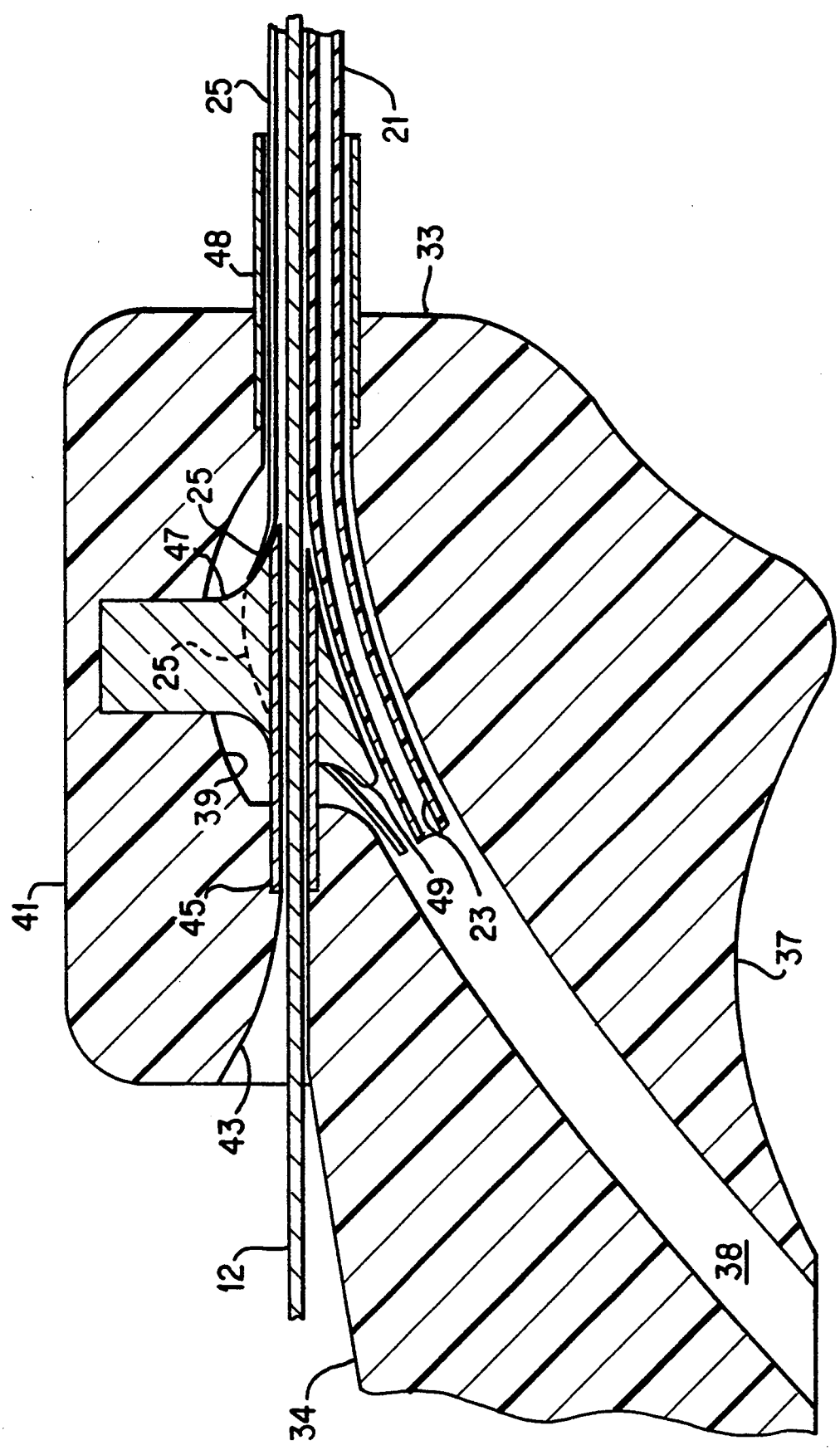
FIG. 4C is a very highly enlarged cross section of a distal section of the DMBAC slide handle.
Figure 5:
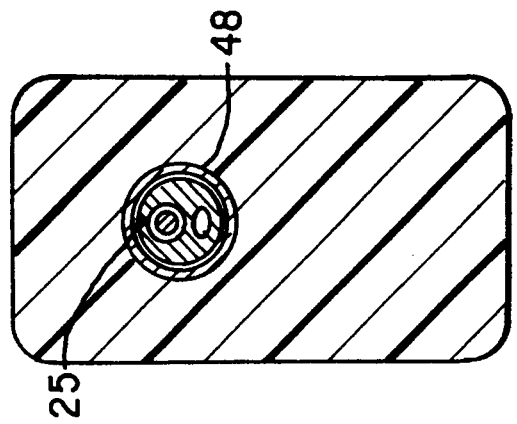
FIG. 5 is a highly enlarged transverse cross section of the slide handle of the DMBAC at section 5—5 of FIG. 4A.
Figure 6:
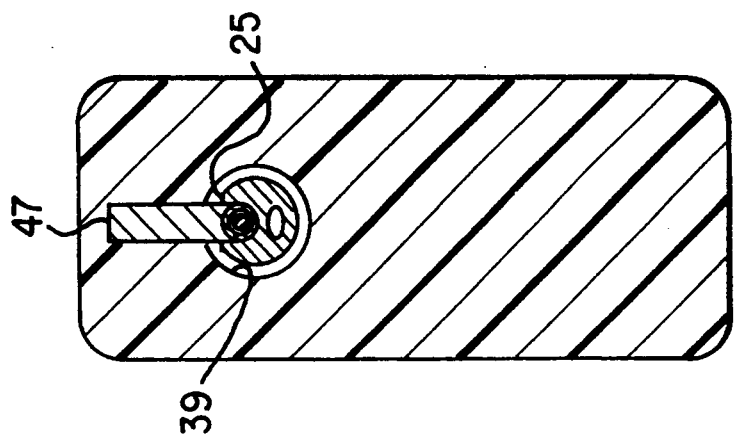
FIG. 6 is a highly enlarged transverse cross section of the slide handle of the DMBAC at section 6—6 of FIG. 4A.

FIGS. 4C and 6 show the open flap 25 of the shaft body 21 as the slit 25 is opened by the tube 45 and the slit opening member 47. A lower slit opening member 49 assists in opening the slit 25 when the shaft body 21 is advanced forward relative to the slide handle 30. The chamber 39 provides a space into which the open flaps of the slit 25 can move in an unconstrained manner. Both slit opening members 47 and 49 have front edges facing the slit that come to a point resembling an inverted bow of a boat. This shape assists in opening of the slit 25 when there is relative motion of the shaft body 21 and the slide handle 30.

Figure 7:
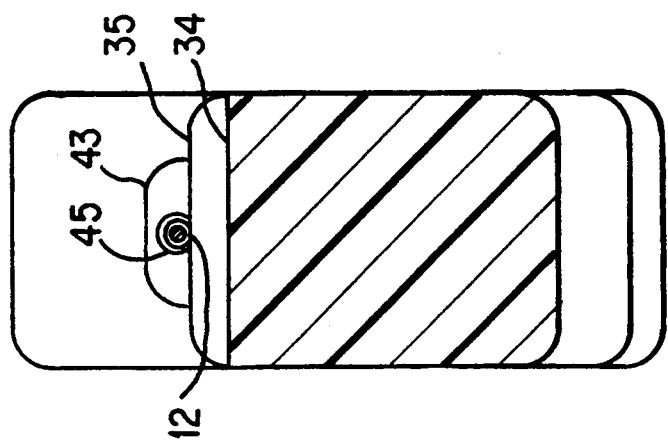
FIG. 7 is a highly enlarged transverse cross section of the slide handle of the DMBAC at section 7—7 of FIG. 4A.

FIG. 7 shows the guide wire 12 as it passes over the ridge 35. Forward or backward motion of the guide wire 12 can be accomplished if the top surface 34 of the handle 30 is entirely flat or somewhat concave. However, the ridge 35 makes thumb initiated motion of the guide wire 12 somewhat more efficient. FIG. 4C and 7 also show that the port 43 has a tapered entry in both the vertical and horizontal planes. This is also true for the ports 42 and 44. These tapered entry and exit ports ease the placement of the guide wire 12 as either the distal end or proximal end of the guide wire 12 is placed through these holes.

The materials of the guide wire 12 and the distal segment 50 are well known in the art of PTCA balloon catheters and guide wires. The shaft body 21 would be made from a somewhat flexible elastomer such as Nylon, polyurethane, polyethylene, Surlyn, etc. The slide handle 30 would typically be molded from a comparatively hard plastic such as Teflon or polycarbonate. The material of the thin-walled tubes 45, 48 and 56 would typically be a 300 series stainless steel. The dimensions of a slide handle would typically be 3.5±2 inches long and 1±½ inch in its largest transverse dimension. The outside diameter of the guide wire 12 would be 0.014±0.004 inches. The outside diameter of the shaft body 21 would typically be 0.0045 plus or minus 0.015 inches. The tubes 45 and 56 would typically have a wall thickness of 0.0015 plus or minus 0.0005 inches, and would typically tubes 45 and 56 have a radial clearance of approximately 0.001 inches relative to the outside diameter of the guide wire 12. The length of the guide wire 12 and DMBAC 10 would be typically of that which is used for PTCA balloon catheter systems.

Slide handle designs in which the position of the guide wire 12 and shaft body 21 are interchanged are also envisioned. Furthermore, instead of having a distal metal tube 48 to join onto the "Y" adaptor 60, the slide handle 30 could have a Luer lock fitting that mates with a Luer lock fitting formed onto the Tuohy-Borst fitting 63 of the "Y" adaptor 60 in order to detachably connect the slide handle 30 to the guiding catheter 70. Still further, a slide handle could be designed that has a distal male Luer lock fitting that joins directly to the female Luer lock fitting 72 of the guiding catheter 70. For that design a separate fluid fitting would be provided on the slide handle that allows contrast medium to be injected from a manifold into the guiding catheter 70. For this design, the "Y" adaptor would actually be formed into the distal end of the slide handle.

Although the present invention is well suited for opening stenoses in coronary arteries, it should be understood that the concepts described herein are applicable to other vessels of the human body. Furthermore, although the distal portion 50 shows a coaxial design of ballon angioplasty catheter, it should be understood that other than coaxial designs can be practical.

Various other modifications, adaptations, and alternative designs are, of course possible in light of the above teachings. Therefore, it should be understood at this time that within the scope of the appended claims, the invention may be practiced otherwise than as specifically described herein.

What is claimed is:

1. A balloon angioplasty catheter system for use by a single operator comprising:
    a flexible guide wire;
    an elongated catheter shaft having distal and proximal ends and having a first lumen in fluid communication with an inflatable balloon mounted near the catheter system's distal end and a second lumen adapted to pass the flexible guide wire, the second lumen having a slit extending from near the shaft's proximal end to near the shaft's distal end which distal end is joined to a transition section to which is joined an inflatable balloon; and,
    a slide handle having a guide wire passageway and also a separate catheter shaft passageway, the slide handle having a slit opening means to allow the guide wire to enter the guide wire passageway, the slide handle also having a detachable joining means to detachably join the slide handle to a "Y" adaptor which is itself detachably joined to a guiding catheter.

2. The balloon angioplasty catheter system of claim 1 wherein the slide handle has two separate passageways for the guide wire and a space between the two passageways where the guide wire lies just outside an outer surface of the slide handle where the guide wire can be manipulated by the single operator.

3. The balloon angioplasty catheter system of claim 2 wherein there is a ridge situated between the guide wire and the outer surface of the slide handle so as to enhance the manipulation of the guide wire by a finger of the single operator.

4. The balloon angioplasty catheter system of claim 1 wherein the slide handle has a distal metal tube through which the catheter shaft passes which metal tube is adapted to be detachably joined to a Tuohy-Borst fitting of the "Y" adaptor.

5. The balloon angioplasty catheter system of claim 1 wherein at the distal end of the slide handle is a Luer lock fitting adapted to be detachably joined to a mating Luer lock fitting on the "Y" adaptor.

6. The balloon angioplasty catheter system of claim 1 wherein the guide wire passageway in the slide handle is a straight passageway so as to optimize guide wire torquing.

7. A single operator, dual modality balloon angioplasty catheter system comprising:
    a flexible guide wire;
    a balloon angioplasty catheter having a first and proximal catheter segment having distal and proximal ends and further having a guide wire lumen through which the guide wire can pass and further having a fluid lumen through which can pass balloon inflation/deflation fluid, the guide wire lumen having a slit which extends longitudinally for most of the length of the balloon angioplasty catheter; the balloon angioplasty catheter also having a second and distal catheter segment having a proximal end joined to the distal end of the first segment and an inflatable balloon situated near its distal end, the second segment having one lumen through which the guide wire can pass and a second lumen in fluid communication with the interior of the balloon and also in fluid communication with the fluid lumen of the first catheter segment; and,
    a slide handle adapted to be moved slideably relative to the first catheter segment, the slide handle having a passageway for the catheter's first segment and also having a thin-walled tube whose distal end can enter the guide wire lumen of the first segment, the tube having slit opening means to open the slit in the guide wire lumen and have the guide wire pass through the tube as the slide handle is moved slideably relative to the proximal segment; the slide handle also having removable attachment means for removably attaching the slide handle to the proximal end of a "Y" adaptor that is itself removably attached to the proximal end of a guiding catheter.

* * * * *